United States Patent

Chan

[11] Patent Number: 5,583,337
[45] Date of Patent: Dec. 10, 1996

[54] APPARATUS AND METHOD FOR INSPECTING HOT GLASS CONTAINERS

[75] Inventor: John P. Chan, Beverley, England

[73] Assignee: Electronic Automation Limited, Hull, England

[21] Appl. No.: 430,830

[22] Filed: Apr. 28, 1995

[30] Foreign Application Priority Data

Apr. 28, 1994 [GB] United Kingdom ............... 9408446

[51] Int. Cl.$^6$ .................................................. G01N 21/90
[52] U.S. Cl. ................................. 250/330; 250/359.1
[58] Field of Search ............................. 250/330, 359.1, 250/360.1, 340

[56] References Cited

U.S. PATENT DOCUMENTS 3,791,741  2/1974  Brenholdt ........................... 250/223 B
3,968,368  7/1976  Sager ................................. 250/340
4,064,534  12/1977 Chen et al. ....................... 250/559.22

FOREIGN PATENT DOCUMENTS 5157523  6/1993  Japan .
1523366  8/1978  United Kingdom .
2096763  10/1982 United Kingdom ............... 250/223 B

*Primary Examiner*—Carolyn E. Fields
*Attorney, Agent, or Firm*—Burns, Doane, Swecker & Mathis, L.L.P.

[57] ABSTRACT

An apparatus for the inspection of hot glass containers for faults comprises a camera (1) sensitive to infrared radiation located opposite the path of travel of the hot glass container (6) through an inspection zone (13). The image of each hot glass container is processed by electronic means (2) into regions and the data for each region is compared with predetermined parameters to determine whether or not the glass container is defective.

18 Claims, 5 Drawing Sheets

RESULTS.
1. CALLIPER D & E – DIAMETER
2. WINDOW D – THRESHOLD SCORE (PIXEL COUNT)
3. WINDOW D – GREYSCALE VARIANCE
4. WINDOW E – THRESHOLD SCORE (PIXEL COUNT)
5. WINDOW E – GREYSCALE VARIANCE.

RESULTS.
1. CALLIPER F – DIAMETER.
2. WINDOW F – THRESHOLD SCORE (PIXEL COUNT).
3. WINDOW F – GREYSCALE VARIANCE.

RESULTS.
1. WINDOW G — GRADIENT SCORE.

WINDOW G
(Href: D, Vref: F).

RESULTS.
1. CALLIPER F — CALLIPER C = DIFFERENCE

APPARATUS AND METHOD FOR INSPECTING HOT GLASS CONTAINERS

BACKGROUND OF THE INVENTION

The present invention generally relates to an apparatus and method for the inspection of newly formed hot glass containers for faults. More particularly, the present invention relates to an apparatus and method in which the heat radiation or infrared (IR) self luminance of the hot glass containers is sensed for inspection purposes. Using the apparatus and method of the present invention both dimensional faults and glass distribution faults can be detected thereby allowing removal of any faulty glass containers from a single file stream of containers. Furthermore, by analysing trends for the performance of each of a plurality of hot glass moulding cavities employed in a bottle forming machine it is possible to warn of incipient faults developing in any one of the cavities.

After formation in a bottle forming machine glass containers are transported in single file on a conveyor to an annealing lehr. Within the bottle forming machine there may be several glass shaping cavities, each of which shape globules of molten glass into their final form. The length of a bottle forming production line is generally such that many faulty glass containers may be made within a particular glass shaping cavity before the first of these glass containers exits the annealing lehr. Therefore, it is desirable to be able to identify a faulty glass shaping cavity as quickly as possible, so as to avoid the production of large numbers of faulty glass containers.

GB 1523366 discloses an apparatus and method for the inspection of newly formed glass containers as they proceed from a bottle forming machine towards an annealing lehr. The apparatus comprises two pairs of heat radiation sensors which are located opposite the path of travel of the glass containers between the bottle forming machine and the annealing lehr. These sensors generate individual signals in response to the heat radiation from a glass container and if the signals do not occur in a predetermined pattern the glass container is rejected as being defective.

The apparatus and method of GB 1523366 enable glass containers to be rejected which are grossly mis-shaped or which have fallen over on the conveyor or which have stuck to an adjacent glass container. However, small faults in the glass containers, and particularly solid inclusions in the side walls of the glass containers, may go unnoticed. More especially it is not possible to determine when faults in the glass containers are caused by incipient faults developing within a particular glass shaping cavity in the bottle forming machine.

It is an object of the present invention to provide an apparatus and method for the inspection of newly formed glass containers which will detect dimensional and glass distribution faults.

It is yet another object of the present invention to provide an apparatus and method for the inspection of newly formed glass containers which analyses the performance trend of each glass shaping cavity and which is thereby able to warn of any incipient faults developing within a cavity.

According to a first aspect of the present invention there is provided an apparatus for the inspection of hot glass containers comprising an inspection zone, a camera sensitive to infrared radiation located opposite the path of travel of the hot glass containers through the inspection zone and electronic means for dividing the image of each hot glass container captured by the infrared camera into regions and for comparing data obtained for each region with predetermined parameters to determine whether or not the glass container is defective.

According to a second aspect of the present invention there is provided a method for the inspection of hot glass containers wherein the hot glass containers are viewed by an infrared sensitive camera as they move through an inspection zone, the image of each hot glass container captured by the infrared camera is divided into a plurality of regions and data from each region is compared with predetermined parameters to determine whether or not the glass container is defective.

Within each region two measurement tools are used, namely "calliper" and "window". The calliper measurements determine the distance between distinct edges of the hot glass container or between one edge and another calliper serving as a reference. The window measurements determine both the relative brightness and the grey scale variance of the hot glass container.

In a preferred embodiment of the present invention a "teach" mode is provided in which the image viewed by the infrared camera is initially inspected by an operative who passes or rejects the glass containers according to whether they appear to be acceptable. Certain "taught" parameters of the acceptable glass containers are stored to provide the predetermined parameters with which further glass containers are compared and any that deviate from these stored predetermined parameters are rejected as being defective. Conveniently, the "taught" parameters are stored on a per-cavity basis and only containers from that cavity are compared with these parameters during inspection.

Preferably, the output of the bottle forming machine is synchronised with the inspection apparatus so that the performance of each glass shaping cavity can be monitored and a warning given of any incipient faults developing within a particular cavity. Conveniently, this is achieved by dividing the bottle forming machine cycle (one cycle is defined as the period taken for all the glass shaping cavities to form a bottle) into a number of time slots, one for each cavity and then synchronising the inspection apparatus to the cavity sequence. In this way it is possible to know from which cavity a bottle has come as it passes before the infrared camera.

As stated the camera image is formed by sensing the IR radiation emitted by the hot glass container. The brightness of the camera image is therefore a function of the amount of IR radiation emitted by the container in view, which in turn is a function of the temperature and amount of glass in the field of view. The use of IR self-luminance means that no additional artificial lighting is required. Furthermore, it can be used to sense coloured or opaque glass with the same degree of image quality as flint (clear) glass.

An important part of the apparatus and method of the present invention is, therefore, its ability to sense and inspect hot glass containers without the use of additional or artificial illumination, for clear, coloured and opaque glass.

SUMMARY OF THE INVENTION

An embodiment of the present invention will now be described, by way of example, with reference to the accompanying drawings, in which:

DETAILED DESCRIPTION

Figure 1:
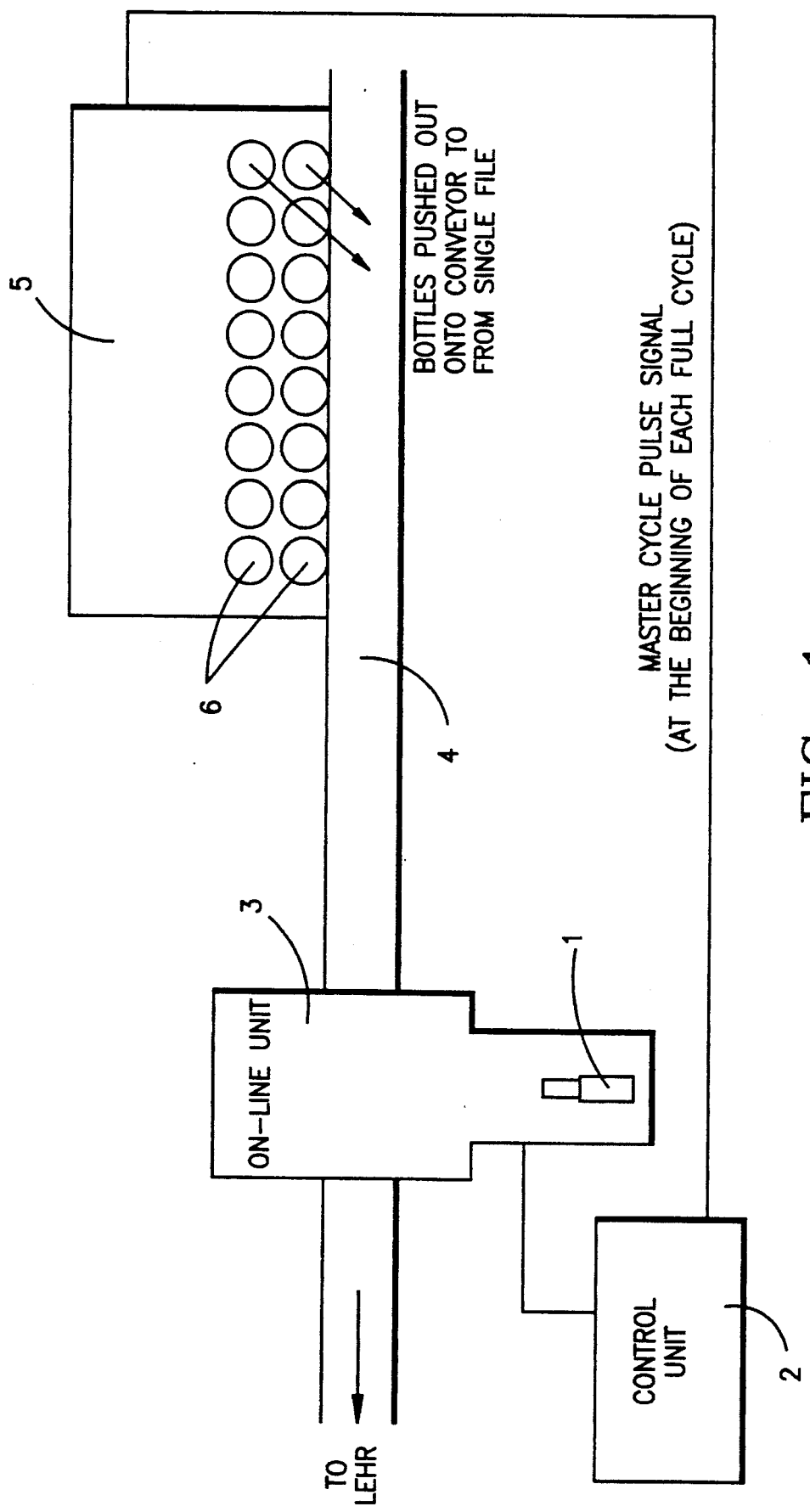
FIG. 1 shows a schematic view of the apparatus of the present invention.

FIG. 1 illustrates the apparatus of the present invention which essentially comprises an infrared camera 1 connected to an electronic control unit 2 which comprises information processing electronics and software. The infrared camera 1 is mounted in an online unit 3 and is positioned opposite a conveyor 4 carrying hot glass containers from a bottle forming machine 5 to a cooling lehr (not shown). The bottle forming machine 5 comprises a plurality of glass shaping cavities 6. Bottles formed within these cavities 6 are pushed out onto the conveyor 4 to form a single uniformly spaced file. The control unit 2 is connected to the bottle forming machine 5 to ensure that the output of the infrared camera 1 is synchronised with the operation of the glass shaping cavities 6.

The operation of the infrared camera 1 is synchronised with that of the glass shaping cavities 6 by monitoring the master pulse signal which initiates each operating cycle of bottle forming machine 5. This cycle is divided into a number of time slots, one for each cavity, so that at any given time it is possible to determine from which cavity 6 a bottle viewed by the infrared camera 1 has come. This is explained further hereinbelow.

The output of the infrared camera 1 is constantly sampled by the software associated with the electronic controller 2 to see if it has changed sufficiently to signify the presence of a glass container in the viewing field thereof and start the inspection process.

Figure 3:
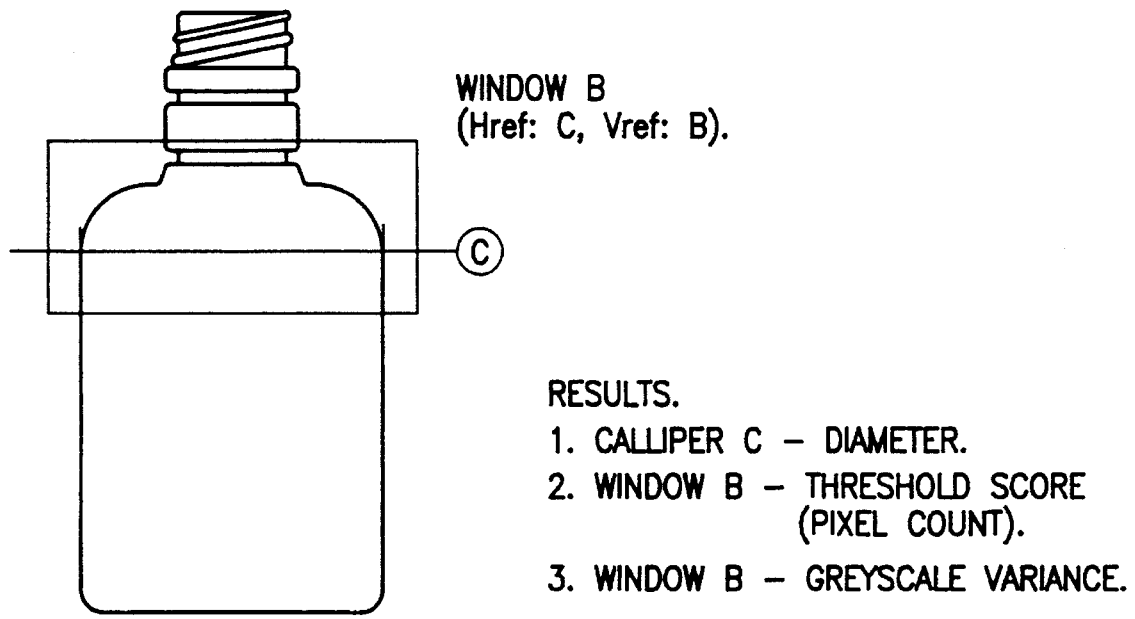
Figure 4:
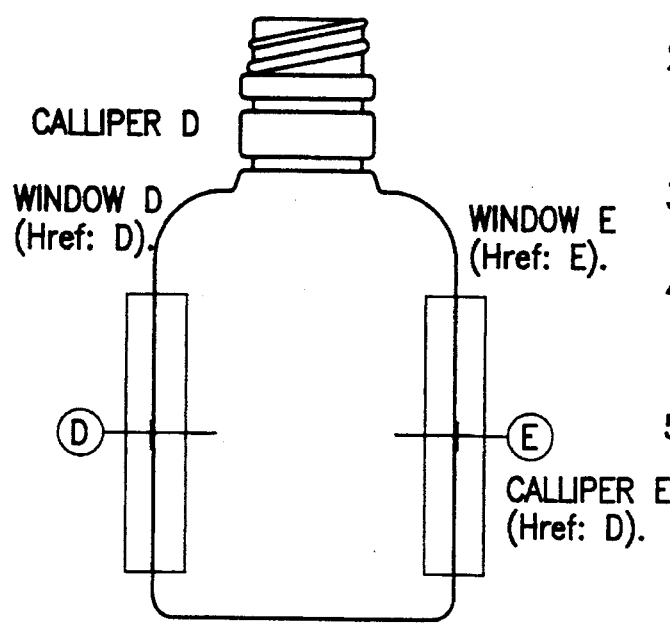
Figure 5:
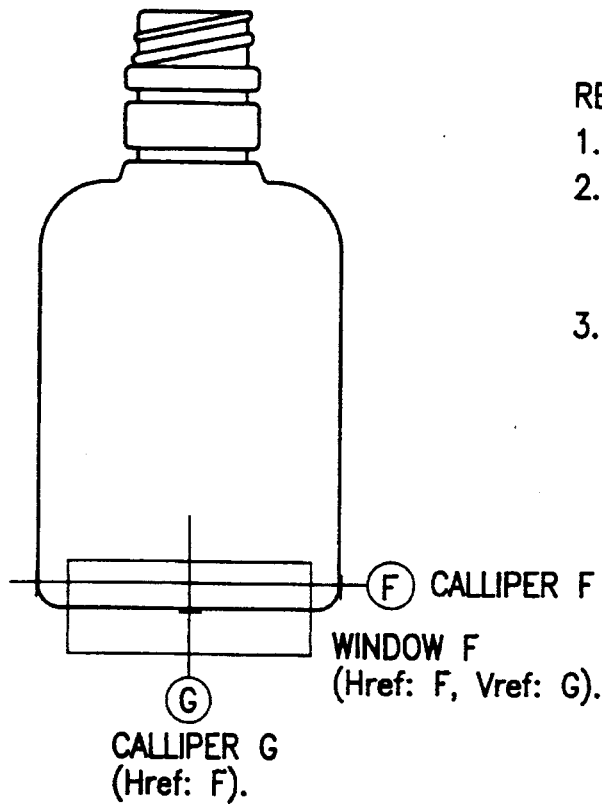
Figure 6:
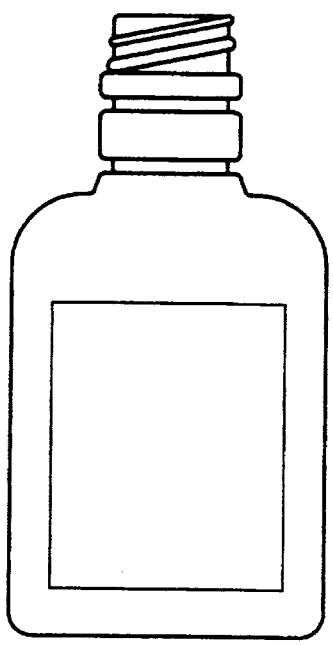
Figure 7:
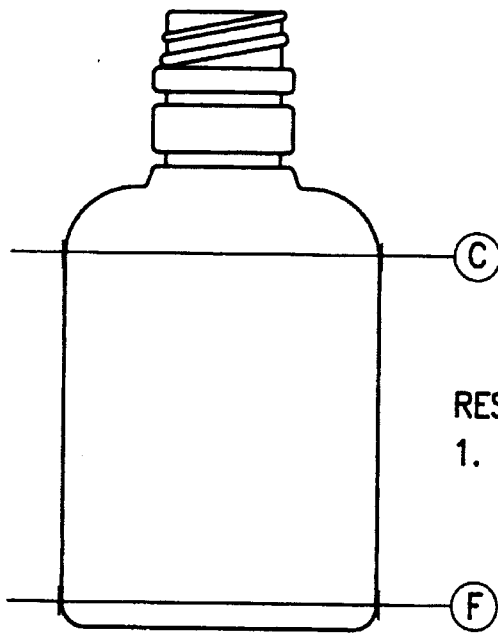

For inspection purposes the information processing software divides the image of the glass container captured by the infrared camera into inspection regions. For a bottle such as the one illustrated in FIGS. 2 to 5 the inspection regions comprise the neck (FIG. 2), shoulder (FIG. 3), sidewalls (FIG. 4), base (FIG. 5), body (FIG. 6) and sidewall verticality (FIG. 7). Within each region two measurement tools are used, namely "calliper" and "window".

Callipers are used for two purposes:

i. To measure the distance between two points on the image and thereby ensure that the dimensional parameters of the glass container fall within predetermined parameters.

ii. Locating and referencing to an edge in order to accurately position windows and other callipers.

Windows are also used for two purposes:

i. To measure the size of relative bright areas within the window.

ii. To determine the grey scale variance from the overall average of all used windows in the image.

Optical callipers function by finding distinct edges due to abrupt changes in image intensities. Once an edge is found, its position is compared with a taught reference. A glass container will pass the calliper measurement only if the difference between the taught and the measured values is less than a preset tolerance.

Inspection windows function by measuring the area of localised bright or dark regions within the window. The area is compared with a taught reference. Again, a glass container will pass the window only if the difference between the taught and measured values is less than a preset tolerance.

The windows also enable grey scale variance calculations to be made. This is done by calculating the average grey scale variance of a window from the overall average of a predefined group of windows. The variance measured within a window for a bottle under inspection is then compared with this taught average grey scale variance and the bottle is only passed if the difference between the two values is within preset tolerances.

The glass distribution algorithm measures changes in brightness levels in regions of the container in relation to other regions. It is therefore a measure of the variations in the amount of glass and temperatures within a container.

Figure 2:
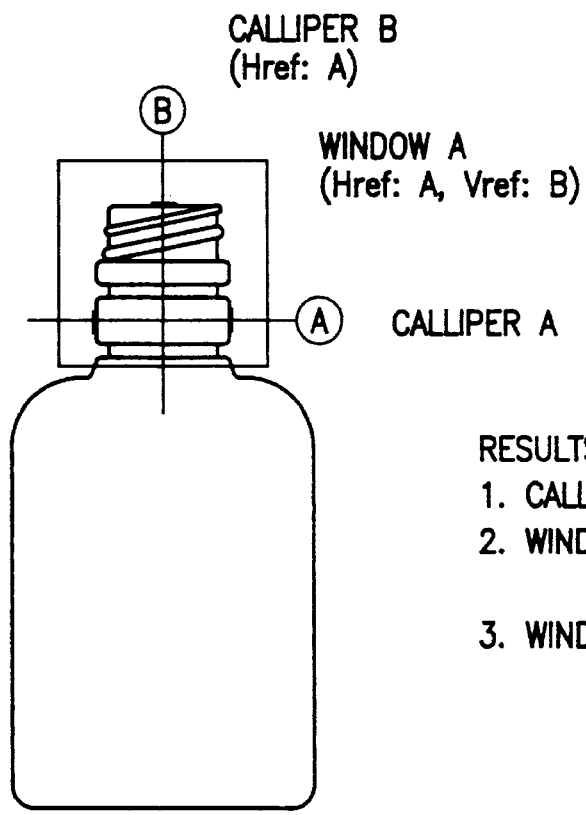
FIGS. 2 to 7 are schematic representations of a glass container as viewed by the infrared camera of the apparatus of the present invention and each illustrates an inspection region of the glass container.

By way of illustrating the purpose of the callipers, calliper B in FIG. 2 determines the position of the top of the bottle, and calliper A measures the diameter of the container at the neck. The neck window (A) is then positioned vertically according to the edge found in calliper B, and horizontally positioned according to the edges found in calliper A. In the diagrams of the inspection regions, "Href: A" means that the horizontal position of the window/calliper is "referenced" to the edge found in calliper A. Likewise, "Vref: B" means that the vertical position of the window/calliper is referenced to calliper B. By segmenting and measuring localised bright or dark spots within a window faults such as 'birdswings' and inclusions may be identified.

Furthermore, distribution of glass in a bottle can be determined by calculating the average greyscale intensity of a window against the overall average. This "variance" is taught on a per-cavity basis and stored in the system memory. During inspection the measured variance is compared with the stored variance. If a window is very bright, compared with the taught figure this implies that there is more glass in the region than is permitted, indicating a glass distribution fault.

Figure 8:
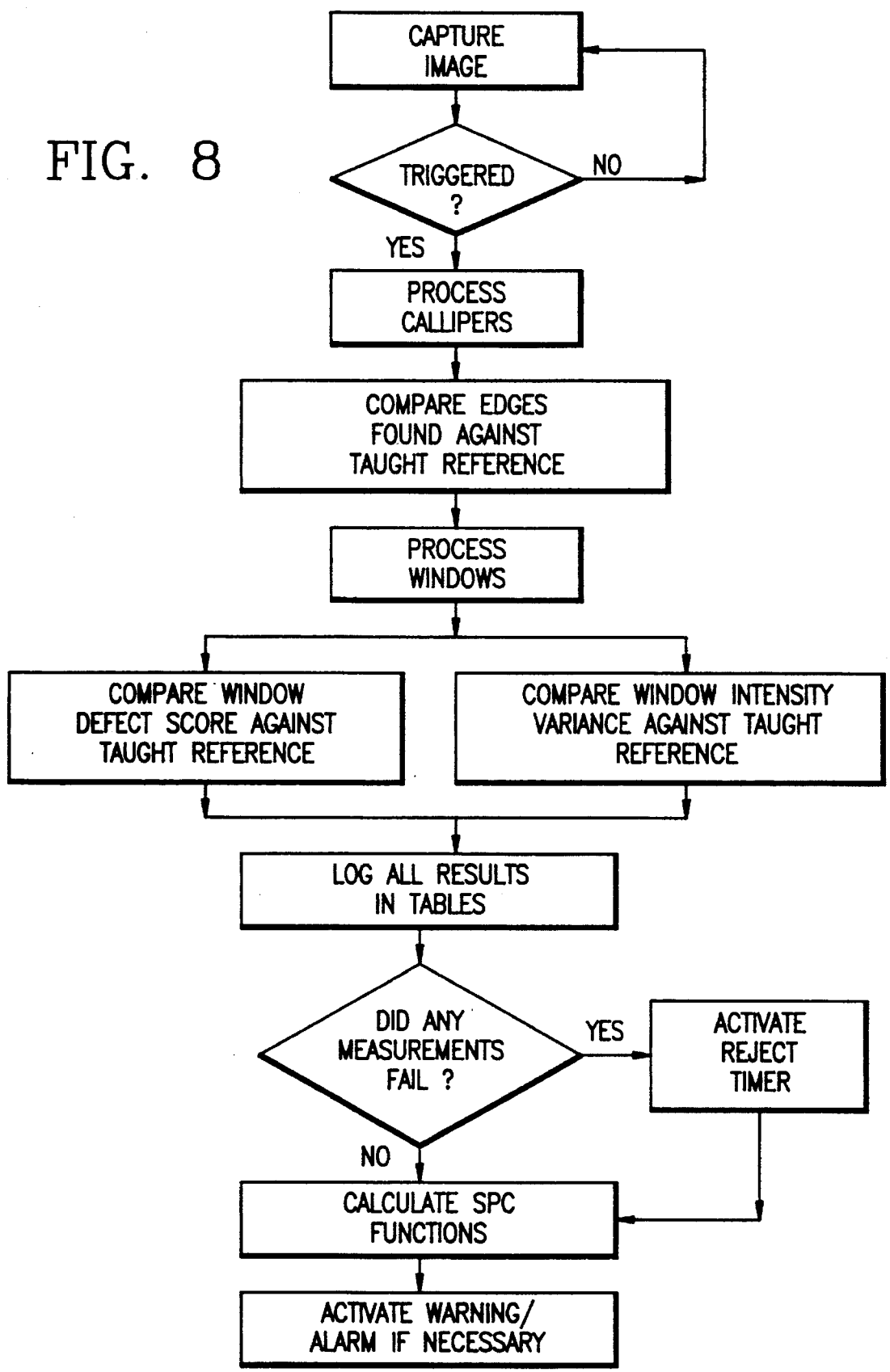
FIG. 8 is a flow chart of the processing performed by the system software for every container passing through the on-line unit.

A summary of the processing steps for inspecting a container is given in FIG. 8.

The electronic control unit 2 is automatically synchronised to the bottle forming machine and is able to track each glass container from the cavity where it was formed to a reject point on the conveyor. This enables the apparatus to inspect and monitor glass containers on a per-cavity basis.

Whenever the master cycle pulse is received from the bottle forming machine the electronic controller 2 resets a master cycle timer and recalculates the cavity start times which are used to measure and gauge which cavity is current in the defined sequence.

The cavity synchronisation procedure is as follows:

1. The apparatus user defines the sequence of cavities passing the infrared camera (e.g. Cavity 8 followed by 5, followed by 11, followed by 3, etc.) The user interfaces with the system via a series of menu options selectable by an industrial light pen. This provides an extremely easy to use yet precise method of setting up and operating the system. The light pen may be removed to prevent unauthorised access to the system.

2. The operator activates the "Sync" option when the first cavity in the defined sequence is about to come into view.

Each time the trigger is activated, the cycle timer value is remembered. This continues for all containers within a full cycle. Once all the trigger times have been gathered, a time slot is allocated for each cavity. The start time for a cavity (n) is given as:

$$C_n = T_{n-1} + (T_n - T_{n-1})$$

Where $C_n$ is the Cavity start time for the nth cavity, $T_n$ is the Trigger time for the nth cavity, $T_{n-1}$ is the Trigger time for the previous (n–1) cavity.

The cavity end time for this cavity is given by the start time of the next cavity.

The system can accommodate for uneven ware spacing, by learning the gaps between the containers via the synchronisation process. Variations in the conveyor speed are also taken into account by automatic readjustments of the expected time slots at every IS cycle.

Whilst learning the ware spacing, certain cavities can be specified as being missing. The system will then automatically allocate a time slot for that cavity, even though no container was detected at the synchronisation stage.

As well as rejecting faulty products, the system software is also able to analyse trends for the performance of each cavity. The information is then used to raise a warning or alarm condition for that cavity.

During runtime, the system software also allows various statistical and graphical information to be displayed:

1. "Graphs"—SPC graphs can be displayed during inspection. This shows the dimension, defect and distribution measurements over the last 250 inspections for a given cavity and container region. Inspection results are displayed as a bar graph with the most recent at the right hand side of the screen.
2. "Table"—AN SPC table can be displayed during inspection. The individual region reject counts are shown for the selected cavity alongside the total for all cavities.
3. "Totals"—This causes an inspection totals summary to be displayed during inspection. Each cavity reject total is shown.
4. "Rejects"—The reject table displays information on the last twenty rejects. The table is automatically updated each time a faulty container is detected. For each reject, the cavity number is shown together with the fault type for each region.
5. "Picture"—This option shows the inspected images of ware passing the camera, together with summary inspection results. The image shown can be "Live" where a live camera image is displayed, or "Reject" where the image of the last reject is displayed.

The system is able to warn off any incipient faults developing on a cavity. This is determined by analysing the last N results from the cavity. If the trend is judged to be approaching the limits of the tolerance for any of the inspection methods, a warning condition is raised.

Alarm and warning levels may be set for each region and each measurement type. The inspection results can be averaged over a number of user-specified cycles, and compared with the warning and alarm limits. This allows the trend to be monitored whilst ignoring individual results.

I claim:

1. An apparatus for inspecting hot glass containers for faults as the containers proceed from a container forming machine to an annealing lehr, comprising:

an inspection zone situated between the container forming machine and the annealing lehr;

an infrared camera located opposite a path of travel of the hot glass containers through the inspection zone for sensing the infrared radiation emitted by each glass container passing through the inspection zone and producing an image thereof the brightness of which is a function of the heat distribution over the hot glass container;

electronic means for dividing the image of each glass container into predetermined inspection regions;

means for determining a grey scale variance of a region from the overall average grey scale intensity of the predetermined inspection regions;

comparator means for comparing the measured grey scale variance of the region with an associated predetermined value; and means for rejecting a glass container if the measured grey scale variance for a region differs from the associated predetermined value by a preset tolerance.

2. The apparatus according to claim 1, further comprising means for determining the size of a localized bright or dark area within a region, comparator means for comparing the measured size of the localized bright or dark area with a predetermined value, and means for rejecting the container if the difference between the measured size of the localized bright or dark area and the predetermined value exceeds a preset tolerance.

3. The apparatus according to claim 2, further comprising electronic calipers for measuring a distance between two points on the image of a glass container provided by the infrared camera, comparator means for comparing the measured distance with a predetermined value, and means for rejecting the glass container if the difference between the measured distance and the predetermined value exceeds a preset tolerance.

4. The apparatus according to claim 1, further comprising electronic calipers for measuring a distance between two points on the image of a glass container provided by the infrared camera, comparator means for comparing the measured distance with a predetermined value, and means for rejecting the glass container if the difference between the measured distance and the predetermined value exceeds a preset tolerance.

5. The apparatus according to claim 4, further comprising a monitor in which the image of a glass container provided by the infrared camera is viewed by an operative, and memory means for storing predefined parameters relating to the grey scale variance, relative brightness, and dimensions of each region for glass containers which are passed as acceptable by the operative to provide the predetermined values with which further glass containers are automatically compared.

6. The apparatus according to claim 5 for use with a container forming machine having a plurality of container forming cavities, further comprising separate memory means for each cavity of the container forming machine such that predefined parameters stored in the separate memory means are specific to a particular cavity, and means for synchronizing an output of the container forming machine with the separate memory means such that the predetermined values associated with a particular cavity are compared with measured parameters of glass containers produced from the particular cavity.

7. The apparatus according to claim 1, further comprising a monitor in which the image of a glass container provided by the infrared camera is viewed by an operative, and memory means for storing predefined parameters relating to the grey scale variance, relative brightness, and dimensions of each region for glass containers which are passed as acceptable by the operative to provide the predetermined values with which further glass containers are automatically compared.

8. The apparatus according to claim 7 for use with a container forming machine having a plurality of container forming cavities, further comprising separate memory means for each cavity of the container forming machine such that predefined parameters stored in the separate memory means are specific to a particular cavity, and means for synchronizing an output of the container forming machine with the separate memory means such that the predetermined values associated with a particular cavity are compared with measured parameters of glass containers produced from the particular cavity.

9. A method for inspecting hot glass containers for faults as they proceed from a container forming machine to an annealing lehr, comprising:

viewing each glass container with an infrared camera as the containers pass through an inspection zone to form an image of each glass container;

dividing the image of a glass container into a plurality of inspection regions;

determining the grey scale variance of a region of the glass container from an overall average grey scale intensity of the regions;

comparing the measured grey scale variance of the region with an associated predetermined value; and rejecting the glass container if the measured grey scale variance differs from the associated predetermined value by a preset tolerance.

10. The method according to claim 9, wherein a size of a localized bright or dark area within a region is compared with a predetermined value and the container is rejected if the difference between the measured size and the predetermined value exceeds a preset tolerance.

11. The method according to claim 10, wherein a distance between predetermined points on the image of the container provided by the infrared camera is measured with electronic calipers, the measured distance is compared with a predetermined distance, and the container is rejected if the difference between the measured distance and the predetermined distance exceeds a preset tolerance.

12. The method according to claim 11, wherein a "teach" mode is provided in which the image viewed by the infrared camera is initially inspected by an operative who passes or rejects the glass containers according to whether they appear to be acceptable, and grey scale variance, relative brightness, and dimension parameters of each region are stored for those containers passed as acceptable to provide the predetermined values with which further glass containers are automatically compared for faults.

13. The method according to claim 12 for use with a container forming machine having a plurality of container forming cavities, wherein the grey scale variance, relative brightness, and dimension parameters are stored on a per-cavity basis and the parameters relating to a particular cavity are used for comparison purposes on containers originating from the particular cavity.

14. The method according to claim 13, wherein an output of the container forming machine is synchronized with an inspection apparatus so that the performance of each cavity of the container forming machine can be monitored and a warning given of any incipient faults developing within a particular cavity.

15. The method according to claim 9, wherein a distance between predetermined points on the image of the container provided by the infrared camera is measured with electronic calipers, the measured distance is compared with a predetermined distance, and the container is rejected if the difference between the measured distance and the predetermined distance exceeds a preset tolerance.

16. The method according to claim 9, wherein a "teach" mode is provided in which the image viewed by the infrared camera is initially inspected by an operative who passes or rejects the glass containers according to whether they appear to be acceptable, and grey scale variance, relative brightness, and dimension parameters of each region are stored for those containers passed as acceptable to provide the predetermined values with which further glass containers are automatically compared for faults.

17. The method according to claim 16 for use with a container forming machine having a plurality of container forming cavities, wherein the grey scale variance, relative brightness, and dimension parameters are stored on a per-cavity basis and the parameters relating to a particular cavity are used for comparison purposes on containers originating from the particular cavity.

18. The method according to claim 17, wherein an output of the container forming machine is synchronized with an inspection apparatus so that the performance of each cavity of the container forming machine can be monitored and a warning given of any incipient faults developing within a particular cavity.

* * * * *